(12) United States Patent
Zucker et al.

(10) Patent No.: US 10,849,691 B2
(45) Date of Patent: Dec. 1, 2020

(54) MINIMALLY INVASIVE INTERVERTEBRAL ROD INSERTION

(71) Applicant: MAZOR ROBOTICS LTD., Caesarea (IL)

(72) Inventors: Edo Zucker, Tel Aviv (IL); Moshe Shoham, Hoshaya (IL); Yuval Chen, Tel Aviv (IL)

(73) Assignee: MAZOR ROBOTICS LTD., Caesarea (IL)

( * ) Notice: Subject to any disclaimer, the term of this patent is extended or adjusted under 35 U.S.C. 154(b) by 0 days.

(21) Appl. No.: 16/312,296

(22) PCT Filed: Jun. 23, 2017

(86) PCT No.: PCT/IL2017/050699
§ 371 (c)(1),
(2) Date: Dec. 22, 2018

(87) PCT Pub. No.: WO2017/221257
PCT Pub. Date: Dec. 28, 2017

(65) Prior Publication Data
US 2019/0231435 A1 Aug. 1, 2019

Related U.S. Application Data

(60) Provisional application No. 62/353,780, filed on Jun. 23, 2016.

(51) Int. Cl.
*A61B 34/10* (2016.01)
*A61B 17/70* (2006.01)
(Continued)

(52) U.S. Cl.
CPC .............. *A61B 34/10* (2016.02); *A61B 17/70* (2013.01); *A61B 17/7013* (2013.01);
(Continued)

(58) Field of Classification Search
CPC ......... A61B 34/10; A61B 34/20; A61B 17/70; A61B 17/7013; A61B 17/7077;
(Continued)

(56) References Cited

U.S. PATENT DOCUMENTS

| 5,343,385 A | 8/1994 | Joskowicz et al. |
| 5,992,210 A | 11/1999 | Blurton-Jones |

(Continued)

FOREIGN PATENT DOCUMENTS

| WO | WO 2012/062464 | 5/2012 |
| WO | WO 2019/043426 | 3/2019 |
| WO | WO 2019/185757 | 10/2019 |

OTHER PUBLICATIONS

Corresponding PCT application PCT/IL2017/050699—Search report and written opinion dated Sep. 25, 2017, already uploaded by USPTO on Dec. 21, 2018.

(Continued)

*Primary Examiner* — Eduardo C Robert
*Assistant Examiner* — David C Comstock
(74) *Attorney, Agent, or Firm* — Sheridan Ross P.C.

(57) ABSTRACT

A system and method for the minimally invasive insertion of an intervertebral rod into the vertebrae of a subject, according to a preoperative surgical plan also defining positions for the insertion of rod clamping screws into the vertebrae. The rod shape for connecting the heads of the screws is calculated, and a path planning algorithm used to determine whether the distal end of the rod can be threaded through the screw heads by longitudinal and rotational manipulation of the proximal end of the rod. If so, instructions are provided for forming that rod shape and for the robotic insertion of the screw holes and the rod. If not, either or both of the screw positions and the rod shape are adjusted, to moderate the bends in the rods, until insertion becomes possible. The (Continued)

insertion can be performed robotically, or, if a navigation tracking system is added, manually.

18 Claims, 4 Drawing Sheets

(51) Int. Cl.
| | |
|---|---|
| *A61B 34/20* | (2016.01) |
| *A61B 17/56* | (2006.01) |
| *A61B 90/00* | (2016.01) |
| *A61B 34/30* | (2016.01) |
| *A61B 17/00* | (2006.01) |

(52) U.S. Cl.
CPC ...... *A61B 17/7077* (2013.01); *A61B 17/7089* (2013.01); *A61B 34/20* (2016.02); *A61B 2017/00238* (2013.01); *A61B 2017/564* (2013.01); *A61B 2017/568* (2013.01); *A61B 2034/104* (2016.02); *A61B 2034/107* (2016.02); *A61B 2034/108* (2016.02); *A61B 2034/2055* (2016.02); *A61B 2034/2063* (2016.02); *A61B 2034/2065* (2016.02); *A61B 2034/2072* (2016.02); *A61B 2034/301* (2016.02); *A61B 2090/376* (2016.02); *A61B 2090/3945* (2016.02); *A61B 2090/3983* (2016.02)

(58) Field of Classification Search
CPC .......... A61B 17/7089; A61B 2034/104; A61B 2034/107; A61B 2034/108; A61B 2034/2055; A61B 2034/2063; A61B 2034/2065; A61B 2034/2072; A61B 2034/301; A61B 2090/376; A61B 2090/3945; A61B 2090/3983; A61B 2017/00238; A61B 2017/564; A61B 2017/568
USPC .................................................. 606/262, 279
See application file for complete search history.

(56) References Cited

U.S. PATENT DOCUMENTS

| | | | |
|---|---|---|---|
| 6,035,691 A | 3/2000 | Lin et al. | |
| 6,235,028 B1 | 5/2001 | Brumfield et al. | |
| 6,253,595 B1 | 7/2001 | Lewis, Jr. | |
| 8,002,798 B2 | 8/2011 | Chin et al. | |
| 8,177,817 B2 | 5/2012 | Fallin | |
| 8,549,888 B2 | 10/2013 | Isaacs et al. | |
| 8,607,603 B2 | 12/2013 | Justis et al. | |
| 8,845,649 B2 | 9/2014 | Jackson | |
| 8,894,655 B2 | 11/2014 | Fallin | |
| 8,979,862 B2 | 3/2015 | Barry et al. | |
| 9,003,859 B2 | 4/2015 | Paris et al. | |
| 9,039,772 B2 | 5/2015 | Park et al. | |
| 9,173,692 B1 | 11/2015 | Kaloostian | |
| 9,271,857 B2 | 3/2016 | Pool et al. | |
| 9,398,925 B2 | 7/2016 | Kiester | |
| 9,421,596 B2 | 8/2016 | Barry et al. | |
| 9,439,692 B1 | 9/2016 | Schlesinger et al. | |
| 9,636,162 B2 | 5/2017 | Isaacs | |
| 9,730,739 B2 | 8/2017 | Taylor et al. | |
| 10,070,936 B2 | 9/2018 | Fallin | |
| 10,136,929 B2 | 11/2018 | Fallin et al. | |
| 10,188,480 B2 | 1/2019 | Scholl et al. | |
| 10,194,957 B2 | 2/2019 | Rouge et al. | |
| 10,194,968 B2 | 2/2019 | Crawford et al. | |
| 10,390,884 B2 | 8/2019 | O'Neil et al. | |
| 10,396,173 B2 | 8/2019 | Rogers et al. | |
| 10,398,481 B2 | 9/2019 | Goel et al. | |
| 10,405,908 B2 | 9/2019 | Redmond | |
| 10,405,935 B2 | 9/2019 | McGahan et al. | |
| 10,433,893 B1 | 10/2019 | Scholl et al. | |
| 10,449,006 B2 | 10/2019 | Dace | |
| 10,492,838 B2 | 12/2019 | Fallin et al. | |
| 2003/0004512 A1 | 1/2003 | Farris et al. | |
| 2003/0055435 A1 | 3/2003 | Barrick | |
| 2005/0033291 A1 | 2/2005 | Ebara | |
| 2005/0085714 A1 | 4/2005 | Foley et al. | |
| 2005/0240078 A1 | 10/2005 | Kwon et al. | |
| 2005/0262911 A1 | 12/2005 | Dankowicz et al. | |
| 2006/0009775 A1 | 1/2006 | Dec et al. | |
| 2006/0074418 A1 | 4/2006 | Jackson | |
| 2006/0150698 A1 | 7/2006 | Garner et al. | |
| 2006/0150699 A1 | 7/2006 | Garner et al. | |
| 2008/0125780 A1 | 5/2008 | Ferree | |
| 2008/0154120 A1 | 6/2008 | von Jako et al. | |
| 2009/0254326 A1 | 10/2009 | Isaacs | |
| 2010/0042154 A1 | 2/2010 | Biedermann et al. | |
| 2010/0152740 A1 | 6/2010 | O'Reilly et al. | |
| 2010/0222822 A1 | 9/2010 | Farris et al. | |
| 2010/0318130 A1 | 12/2010 | Parlato et al. | |
| 2011/0077690 A1 | 3/2011 | Shin et al. | |
| 2011/0270262 A1 | 11/2011 | Justis et al. | |
| 2012/0186411 A1 | 7/2012 | Lodahi et al. | |
| 2012/0232339 A1 | 9/2012 | Csiky | |
| 2013/0345757 A1 | 12/2013 | Stad | |
| 2014/0137618 A1 | 5/2014 | Isaacs | |
| 2014/0303672 A1 | 10/2014 | Tran et al. | |
| 2014/0316420 A1 | 10/2014 | Ballard et al. | |
| 2015/0100091 A1 | 4/2015 | Tohmeh et al. | |
| 2015/0196365 A1 | 7/2015 | Kostrzewski et al. | |
| 2015/0305786 A1 | 10/2015 | Wehrle et al. | |
| 2016/0166335 A1* | 6/2016 | Roger .................... A61B 34/25 606/130 |
| 2017/0056086 A1 | 3/2017 | Kostrzewski et al. | |
| 2017/0135770 A1* | 5/2017 | Scholl ................ G06F 19/3481 |
| 2017/0360493 A1 | 12/2017 | Zucker et al. | |
| 2018/0147018 A1 | 5/2018 | Crawford et al. | |
| 2018/0280147 A1 | 10/2018 | McGahan et al. | |
| 2018/0289408 A1 | 10/2018 | McGahan et al. | |
| 2018/0289491 A1 | 10/2018 | McGahan et al. | |
| 2019/0029737 A1 | 1/2019 | Wall et al. | |
| 2019/0209080 A1 | 7/2019 | Gullotti et al. | |

OTHER PUBLICATIONS

International Search Report and Written Opinion for International (PCT) Patent Application No. PCT/IL2015/051182, dated Mar. 16, 2016, 8 pages.
Partial European Search Report for European Patent Application No. 15866361.7, dated Jul. 12, 2018, 12 pages.
International Search Report and Written Opinion for International (PCT) Patent Application No. PCT/IL2017/050699, dated Sep. 25, 2017, 11 pages.
Official Action for U.S. Appl. No. 15/533,037, dated Apr. 15, 2019, 7 pages.
Notice of Allowance for U.S. Appl. No. 15/533,037, dated Sep. 30, 2019, 5 pages.
U.S. Appl. No. 16/726,720, filed Dec. 24, 2019, Zucker et al.
Extended European Search Report for European Patent Application No. 17814903.5, dated Feb. 13, 2020, 11 pages.

* cited by examiner

MINIMALLY INVASIVE INTERVERTEBRAL ROD INSERTION

CROSS REFERENCE TO RELATED APPLICATIONS

This application is a national stage application under 35 U.S.C. § 371 of PCT Application No. PCT/IL2017/050699, having an international filing date of Jun. 23, 2017, entitled "Minimally Invasive Intervertebral Rod Insertion", which designated the U.S., and which claims the benefits of and priority under 35 U.S.C. § 119(e) to US. Provisional Application Serial No. 62/353,780, filed on Jun. 23, 2016, entitled "Minimally Invasive Intervertebral Rod Insertion."

FIELD OF THE INVENTION

The present invention relates to the field of spinal surgery for intervertebral fusion or for spinal curvature correction, especially as applied to minimally invasive methods of performing such surgery.

BACKGROUND

In spinal correction or fusion surgery, the accurate insertion of spinal vertebral connection rods into the heads of pedicle screws which have been inserted into predetermined positions in the subject's vertebrae, remains a problem for the surgeon. The insertion of the pedicle screws themselves in the accurately planned location can be performed by the use of minimally invasive, robotically guided procedures. With regard to the insertion of the connecting rods, a single level rod insertion can often also be performed minimally invasively, using fluoroscopic images and an insertion device which guides the rod into a single incision point and between the heads or tulips of the pre-inserted pedicle screws. However, for multiple level procedures, the currently generally used procedure is to perform an open procedure where the pedicles and the inserted pedicle screws' tulips are exposed so that the surgeon is able insert the bent connecting rod downwards into the visibly exposed tulips. However it would be very advantageous if a method could be devised for a complete minimally invasive procedure in which insertion of the connecting rods is also performed without the need to make any large incisions other than the minimally invasive punctures at preselected points down the patient's back for accommodating the pedicle screw insertions, and a single additional incision through which the rod is inserted so that it can be woven through the screws' tulips.

There exist prior art methods of insertion of vertebral fusion rods by minimally invasive procedures, such as the SEXTANT™ Percutaneous Rod Insertion Set, as supplied by Medtronics Inc. of Minneapolis, Minn. and as described in U.S. Pat. No. 7,815,664 for "Systems and methods for spinal stabilization with flexible elements". This system is however, limited to an insertion path which is an arc section of a circular path, such that its ability to adapt to complex screw positions and in more than one plane is highly limited, and essentially impossible.

There therefore exists a need for a method for the insertion of vertebral connection rods by minimally invasive procedures, which overcomes at least some of the disadvantages of prior art systems and methods.

The disclosures of each of the publications mentioned in this section and in other sections of the specification, are hereby incorporated by reference, each in its entirety.

SUMMARY

The present disclosure describes a new exemplary method and system for planning and executing the treatment of defective spinal curvature using minimally invasive, robotically maneuvered, vertebral connection rod insertion. The method takes the surgeon's initial preoperative correction plan, and determines the theoretically optimum screw and rod configuration to provide the best correction for the patient's condition. This determination can also include decisions as to perform osteotomies on specific vertebrae, if by so doing, the extent of curvature corrections can be reduced and consequently, the forces of the rod on the vertebrae can be similarly reduced. Conversely, this determination can also include decisions on how to avoid or reduce the need for osteotomies if an acceptable curvature correction can be achieved which may not be the optimal correction, but will provide relief to the patient's condition without the need for osteotomic procedures, which are generally rather invasive. The planning procedure thus involves a compromise between a number of different factors, including:

(i) the need for maintaining minimal forces on the pedicle screws, and hence their associated vertebrae;

(ii) providing an acceptable curvature correction that relieves the patient's condition sufficiently;

(iii) the clinical advantages of performing the entire procedure minimally invasively; and (iv) the minimization or complete elimination of the need for osteotomies if a suitable curvature profile can be achieved without.

In calculating such a surgical plan, use may be made of a comprehensive three dimensional spinal surgical correction software suite, which takes into account a pre-operative analysis of the rigidity and mobility of segments or even individual vertebrae of the subject's spine, such as that described in U.S. Provisional Patent Application No. 62/240,751 for "Global Spinal Alignment Method", having a common inventor with the present application.

Once this theoretically optimal correction plan has been determined, and the required rod shape (for each side of the spine) has been selected, an insertion path calculation algorithm is activated to determine whether it is physically possible to insert the selected rod shape from a single incision point at one end of the spinal region to be corrected, by the use of robotically controlled insertion movements. The robot has to be registered to the positions of the pedicle screws and their heads (tulips), so that these robotically controlled insertion movements are correctly related to the positions of the pedicle screw heads. Such registration can be achieved by mounting the robot base in a predetermined position relative to the subject's vertebrae.

There are a number of methods by which the robot's co-ordinate frame can be registered to that of the positions of the pedicle screws and their heads. According to a first method, the robot can be registered to the preoperative images of the surgeon's correction plan, by comparing intraoperative images including both features of the subject's anatomy and a three dimensional target held by or attached to the robot, with the same features of the subject's anatomy seen in the surgeon's preoperative planning images of the subject. So long as the robot's position relative to the subject's spine is not changed, the registration will remain effective, whether the robot is mounted on the subject's body, or adjacent to the subject with the subject kept immobile relative to the robot position. Other methods utilize a pointer held by the robot and used to touch landmark locations of the subject's spine or anatomy, such that the location of those landmarks are registered to the co-ordinate system of the robot. Another method may use an external navigation system which can be used to define the positions of markers attached to the robot or to its activated arm when in a known pose, and the same navigation subsystem can be used to define the position of a hand held pointer touching body parts of the subject, such as exposed pedicle screws or attachments thereto or any other predefined feature, thereby relating the robot frame of reference to that of the body parts of the subject.

Such robotic manipulation can move the end of the rod in three dimensions and can rotate the rod. These motions should be such that the distal end of the rod will pass through, or pass close to all of the pedicle screw heads along the region to be corrected, so that when completely inserted, the rod will sit in its preplanned position within all of the required screw heads. The pedicle screw towers, which are rigidly attached to the pedicle screw heads and protrude above the surface of the subject's skin, can be used to slightly manipulate each vertebra as the leading end of the inserted rod reaches each pedicle screw head, to ensure that the rod passes through the screw head if the planned rod shape has not succeeded in enabling the rod end to be exactly aligned with each screw head tulip. Such vertebral manipulation can be performed manually by the surgeon, even if the entry itself is performed robotically. Obviously, there is a limit to the extent to which the vertebrae can be shifted to accommodate the advancing rod, since excessive forcing would exert excessive stress on the vertebral joints, thereby defeating part of the purpose of the procedure. Typically, motion over a range of up to 2 to 3 mm can be attempted. To assist in the rod insertion and alignment procedure, the leading end of the rod should optimally have a sharpened or rounded profile. The towers protruding from the pedicle screws are such that the rod can be positioned in the slots in the towers but above the tulip, and its position adjusted before the rod is pushed downwards between the slots in the towers and into the tulips.

As an alternative to the above described robotic insertion of the rod, it may be possible for the surgeon to insert the rod manually, using for guidance, an external navigation system which tracks the position and orientation of the rod by means of beacons attached to its exposed end, and compares that position and orientation with preoperative information regarding the desired trajectory of the rod based on the surgeon's preoperative insertion plan. As a further alternative, the navigation system can be used to directly track both the position and orientation of the rod during insertion, and the three dimensional position of the pedicle screws or attachments thereto, as already defined by the preoperative plan.

If the insertion path algorithm shows that the selected rod cannot be inserted in its entirety from one end by a minimally invasive procedure, then an iterative procedure is commenced in which the positions and entry angles of the pedicle screws are changed to the extent that the pedicle structure allows, and the rod shape is recalculated. Additionally, and only if necessary, one or more osteotomies are proposed, together with their planned angular corrections, and the insertion path again virtually attempted using the corrected parameters. This procedure is performed iteratively, with each iteration attempting to achieve a successful insertion procedure for a longer and longer section of the planned spinal correction, using optimized combinations of the various variable factors involved, until a combination configuration is achieved which enables successful insertion of the rod from a single incision, while still providing the required clinical results of the procedure.

Even when a successful insertion configuration has been achieved, further optimization can be performed iteratively, in order to improve the insertion path by reducing the pressure exerted on the patient's tissues, and by reducing the lateral forces exerted by the inserted rod on the pedicle screws. Additionally, although the method had been devised primarily to most readily enable minimally invasive insertion of vertebral connection rods, and osteotomic procedures have been used as a means of assisting this aim, a converse approach is also possible, in which the procedure of parameter selection and insertion path selection may also be performed iteratively with the aim of minimizing the need for osteotomies. Since an osteotomy procedure and the access thereto is substantially more invasive than the incisions for screw placement or rod insertion, reduction in the number of osteotomies required for a specific correction procedure may be a more advantageous result than a more favorable insertion path which could be achieved with more osteotomies. The particular approach used will be determined by the surgeon taking into account all of the subjective and objective particulars of each case.

The system and methods of the present disclosure thus enable the achievement of a global correction procedure for spinal curvature defects or for spinal decompression, which uses iterative adjustments to the screw positions, rod shapes and possible osteotomy procedures to enable percutaneous insertion of the connection rod or rods to be performed, thereby often saving the patient the substantial trauma of open back surgery.

There is thus provided in accordance with an exemplary implementation of the devices described in this disclosure, a method of planning an intervertebral rod insertion procedure, comprising:

(i) using a preoperative surgical plan to define positions for inserting screws into vertebrae of a subject, (ii) calculating the shape of a rod that will connect the heads of the screws, (iii) using a path planning algorithm to determine whether the manipulating of a proximal end of the rod having the calculated shape, enables the distal end of the rod to pass sequentially through the heads of the screws, (iv) if the distal end of the rod can be passed sequentially through the heads of the screws, providing instructions for the insertion of the screws in the defined positions, providing information for forming the rod having the shape, and providing instructions for the insertion of the rod, (v) if the distal end of the rod cannot be passed through the heads of the screws, adjusting in the plan, at least one of the position and orientation of at least one of the screws in order to moderate bends in a path between the heads of the screws, and recalculating the shape of the rod to match the adjusted positions and orientations of the screws, (vi) using the path planning algorithm on the rod having moderated bends to determine whether the rod can be passed through the heads of the screws, and (vii) repeating the steps of adjusting the screw positions, and adjusting the rod shape, until the rod acquires a planned shape that enables it to be inserted between the heads of the screws by longitudinal manipulation of the rod from its proximal end.

In such a method, the step of determining whether manipulating a proximal end of the rod having the calculated shape enables the distal end of the rod to be passed through the heads of the screws, may include broadening the range by which the rod is passed through the heads of the screws by enabling adjustment of the position or orientation of at least one of the vertebrae. Additionally, the criterion of enabling the distal end of the rod to be passed through the heads of the screws may include the possibility of proposing adjustment of the position or orientation of at least one of the vertebrae.

According to a further aspect of these methods, the plan may further include the optional use of osteotomies on selected vertebrae to enable the moderating of bends in the rod. Such moderating of bends in the rod may comprise the reduction of at least one of the extent and the diversity of direction of the bends. In methods of the optional use of osteotomies, at least some of the number, position and parameters of the osteotomies may be selected to enable achievement of a rod having a shape incorporating bends which enable it to be minimally invasively inserted between the heads of the screws. Such a shape enabling the rod to be inserted minimally invasively, should be planned to have a reduced diversity of bend directions.

Additionally, according to yet another implementation of the above described methods, the method may further comprise the step of providing instructions to a robot control to manipulate the proximal end of the rod, such that the rod can be inserted robotically. Such instructions may utilize the output of the path planning algorithm.

Any of the previously described methods may further comprise the step of providing instructions to manipulate the proximal end of the rod manually using information from X-ray fluoroscopy images to enable the defining of the position of the rod during insertion.

Alternatively and additionally, the previously described methods may further comprise the use of a navigational tracking system to enable determination of the position and orientation of the proximal end of the rod during insertion. In the latter case, the rod may comprise at least one marker attached with a predetermined pose on the proximal end of the rod, the marker being such that its pose can be tracked by the navigational tracking system during insertion of the rod.

Further implementations of the previously above described methods, in which the distal end of the rod can be passed through the heads of the screws, may comprise the step of determining whether inserting the rod involves motions of the rod within a predetermined threshold of acceptable insertion motion procedures. Furthermore, such further implementations may further comprise the step of determining the maximum lateral forces which the insertion procedure would exert on a patient's tissues.

According to yet further implementations described in the present disclosure, there is provided a system for determining the three dimensional shape of a vertebral insertion rod, comprising:
  (i) a collar threaded on the rod, the collar having dimensions relative to those of the rod such that it can slide along the rod and maintains an orientation coaxial with the section of the rod on which it is situated,
  (ii) at least one marker fixedly attached to the collar, the marker being such that its pose can be tracked by a navigational tracking system, and
  (iii) a control system configured to utilize data from the navigational tracking system to determine the orientation of the collar at each longitudinal location along the rod. Such a system may further comprise at least one marker fixedly attached to the rod, the marker being such that its pose can be tracked by the navigational tracking system, and wherein the control system is configured to utilize data from the navigational tracking system to determine the pose of the at least one marker and hence of the rod, such that the three dimensional shape of the rod can be determined regardless of motion of the rod.

There is yet further provided, a system for the minimally invasive insertion of an intervertebral rod into the vertebrae of a subject, according to a preoperative surgical plan defining positions for inserting rod clamping screws into the vertebrae, the system comprising:
  (i) a robot whose position is known relative to the vertebrae of the subject, and
  (ii) a control system receiving information about the position of the heads of the screws, and information about the calculated shape of a rod planned using a preoperative surgical plan such that it can pass between the heads, the control system being adapted to:
    (a) utilize a path planning algorithm to determine whether manipulating a proximal end of the rod having the calculated shape, enables the distal end of the rod to be passed sequentially through the heads of the screws, and
    (b) if the distal end of the rod can be passed through the heads of the screws, instructing the insertion of the screws in the defined positions, and instructing the robot to insert the rod by longitudinal manipulation of the rod from its proximal end.

In such a system, if the distal end of the rod cannot be passed through the heads of the screws, the control system is further adapted to:
    (c) adjust at least one of the position and orientation of at least one of the screws in order to moderate bends in a path between the heads of the screws, and to adjust the information about the calculated shape of the rod to match the adjusted positions and orientations of the screws,
    (d) use the path planning algorithm on the rod having moderated bends, to determine whether the rod can be passed through the heads of the screws, and
    (e) repeat the steps of adjusting the screw positions, and adjusting the rod shape, until the rod acquires a shape that enables the robot to insert the rod between the heads of the screws by longitudinal manipulation of the rod from its proximal end. In this system, the moderating of bends in the rod may comprise reducing at least one of the extent and the diversity of direction of the bends.

In either of the above-described systems, at least some of the vertebrae may incorporate a tower adjustment device to enable adjustment of the position or orientation of at least one of the vertebrae, such that the control system also enables the broadening of the range by which the rod is passed through the heads of the screws.

Additionally, any of these systems may further comprise a navigational tracking system adapted to enable determination of the position and orientation of the proximal end of the rod during insertion. In such a situation, the rod may comprise at least one marker attached with a predetermined pose on the proximal end of the rod, the marker being such that its pose can be tracked by the navigational tracking system during insertion of the rod. Finally, in any of these described systems, the control system may be adapted to receive information about the position of the rod during insertion using X-ray fluoroscopy images.

BRIEF DESCRIPTION OF THE DRAWINGS

The present invention will be understood and appreciated more fully from the following detailed description, taken in conjunction with the drawings in which.

DETAILED DESCRIPTION

Figure 1:
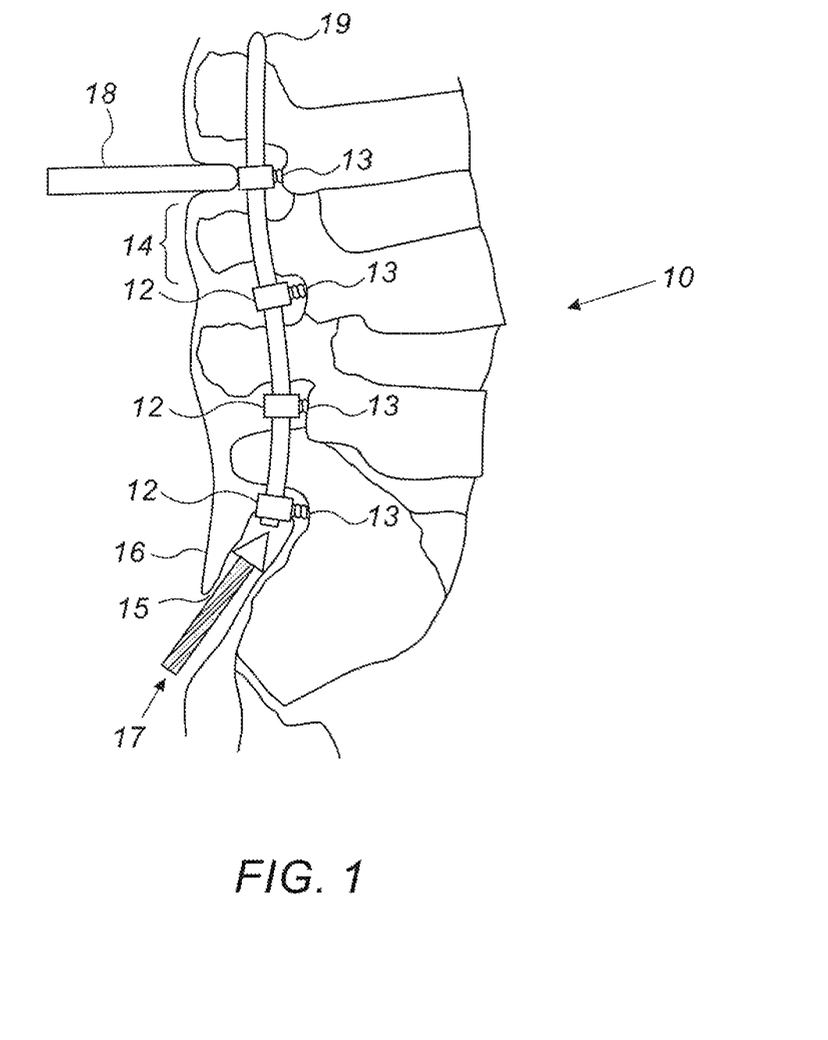
FIG. 1 shows a sagittal plane drawing of a section of the lower spine showing how the vertebral connection rods are fitted between pedicle screws at a number of levels of vertebrae.

Reference is first made to FIG. 1 which shows a typical section of the lower region of a spine 10 showing how a vertebral connection rod 11 is fitted between the tulips 12 of pedicle screws 13 at a number of levels of vertebrae. The example shown in FIG. 1 is a sagittal view of the spine, illustrating the use of a connection rod 11 to correct defective spinal curvature due to lordosis, but it is to be understood that the same considerations would also be applicable for a scoliosis correction procedure in the coronal plane, or any other deformity in two and three-dimensional correction planes.

The optimal positions of the pedicle screws 13 should have been obtained from a preoperative plan determined by the surgeon for correcting the spinal curvature. The screw positions may have been determined and the receiving holes for the screws drilled using robot guidance. Furthermore, the characteristics of the rods have likewise been determined preoperatively, in order to connect the vertebral pedicle screws, either as part of a fixation or fusion procedure, or as part of a spinal curvature correction procedure. The rod characteristics include not only the distance between the fixing points to the pedicle screws, but also the shape of the rod, including any curves necessary in order to match the nonlinear positions of the pedicle screw heads, whether offset laterally or in effective height or orientation angle, or a combination of all these three spatial factors.

The rods may be bent and twisted to the desired shape using any rod bending technique, such as that described in co-pending PCT application No. PCT/IL2015/051182, for "Shaper for Vertebral Fixation Rods" having a common inventor with the present application. In that application, the preoperative plan and the robotically positioned pedicle screws are used as inputs to the bending system to form the rod robotically with the desired three-dimensional shape. Robotic procedures have thus far contributed to the rod insertion procedure in three separate stages:

(i) Defining and executing the pedicle screw positions 13, these being procedures which can be done minimally invasively;

(ii) Defining the bent shape of the rod 11; and (iii) Generating the rod 11 for insertion.

As is observed in the example shown in FIG. 1, although the connecting rod between the lower three pedicle screws 13 is located on a circular section of an arc, which a prior art device such as the SEXTANT™ could insert percutaneously, the required shape of the rod in the region 14 above that level departs from the circular arc path, making it impossible to insert using such a prior art device. Furthermore, the drawing of FIG. 1 only shows the shape of the rod in the plane of the drawing (the sagittal plane), and in practice, the pedicle screws 13 may not generally lie in one plane, but could deviate in the coronal plane also, such that a path which can have bends in two orthogonal directions, i.e. having a composite three dimensional path, may be required to define the optimal rod configuration.

Referring back now to the connecting rod procedure, if, in addition to the three above mentioned steps, it were possible to perform a fourth step of insertion of the rod through the pedicle screw heads using the same robotic guidance and control system (not shown in FIG. 1) as that used for insertion of the screws, and optionally for the planning and shaping of the vertebral fixation rods, the entire procedure could become minimally invasive and robotically controlled, which would be a great advantage in such surgical procedures.

Additionally, when the spinal deformity is so severe that the use of correction rods could not fully correct the curvature to the desired extent, then osteotomy surgery may need to be performed on specific vertebrae in order to enable correction of the curvature using fixation or correction rods. Such osteotomic surgery is not generally performed minimally invasively, but may be so performed in certain limited cases. In any event, an osteotomy performed at one level may enable the spinal curvature to be corrected sufficiently that minimally invasive insertion of the connecting rod now becomes possible, where previous to such surgery, that was impossible. Osteotomies may therefore be performed not only to accomplish more efficient correction of curvature defects in the spine, but also to reduce the need for connection rods to have unusually curved shapes, thereby more readily enabling the entire insertion process to be performed minimally invasively using a robotic insertion procedure. Even though the minimally invasive procedure may necessitate one or more osteotomies, the ability to perform the whole insertion procedure minimally invasively, thereby saving the need for extensive open back surgery, may more than compensate for the trauma which an osteotomy procedure may create on just one or more vertebrae. As previously mentioned, the need for osteotomies, or the ability to avoid osteotomies will be dependent on the clinical state of the subject and the objective ability to improve his/her curvature defects.

In FIG. 1, the minimally invasive rod insertion procedure is shown being performed through a single incision 15 through the patient's skin 16, at a location where the robot (not shown in FIG. 1) will be able to manipulate the rod, as indicated by the arrow 17, along the direction of the spine and into the pedicle screws heads. The sharpened, or at least rounded, front end 19 of the rod 11 should enable this robotic insertion step to be performed with minimal trauma to the tissue en-route.

The shape and length of a vertebral connection rod should therefore be planned in order to fulfill two conditions:

(a) For the case of correction of spinal curvature, such as in scoliosis, lordosis or kyphosis correction, the rod should be shaped such that not only does it efficiently compensate for the curvature, but in addition, results in minimum force being exerted on the rod by the vertebra which it is connected to and which it is attempting to realign.

(b) Secondly, the rod should have a shape which facilitates its insertion by the minimally invasive robotically guided procedure. When multi-level insertion is to be performed, if the insertion is performed minimally invasively, robotic control of the insertion is considered to be almost essential because of the complexity of the motions required at the proximal end of the rod, so that the distal end of the rod passes accurately through the pedicle screw tulips. This enables the procedure to be accomplished without the surgeon needing to perform open back surgery in order to view the rod and screw positions. However, if some form of navigational guidance is used for the rod positioning, as will be discussed below in relation to the method shown in FIG. 3, a manual rod insertion procedure also becomes possible. However, such a procedure may be complex to perform because of the need to visualize the 3-dimensional position of the rod from a number of 2-dimensional fluoroscope images. In addition, such a method would require a significant number of fluoroscope images, so that the position of the rod during insertion can be tracked. This is disadvantageous for the patient and the operating room staff.

In the planning stage of a surgical correction procedure, the scope for adjustment of the position and orientation of the screws is fairly limited, since the position and orientation are limited by the small range of insertion locations in the pedicles, and there is thus little room for selection of an alternative position or orientation, limiting the freedom of selection of screw position. On the other hand, more choice is available for the shape of the fusion or connection rods, which can be bent in three dimensions and twisted using suitable instrumentation. The rod shape and the exact position and orientation of the pedicle screws can be preplanned, (at least as far as the limited entry range into the pedicle makes the latter possible), such that when connected to the screw tulips, the force applied to correct the curvature, and also the force which vertebral motion exerts on the screws, is minimal, yet still fulfils the required spinal correction forces. This optimal selection thereby provides the highest durability of the combined fusion or correction element system.

It is therefore necessary to define the positions of the screws and the length and the shapes of the rods which will result in minimum force being applied, while achieving the curvature correction required. However, the best screw positions and the selected shape of the rod may not be the optimum configuration which would enable simple robotic insertion of the rod percutaneously. In fact, for many screw and rod configurations selected to provide the best surgical correction to the problem, it may be impossible to insert the rod minimally invasively from a single incision, since the selected positions and orientations of the screw heads would not enable such a path to be traced with a rigid rod from a single insertion position. Since there are a limited range of screw positions and a limited range of rod-shapes that can be utilized to perform the correction, it is necessary to perform optimization of the screw positions and the rod shapes in order to find a combination that makes such a percutaneous robotic insertion procedure possible, and, when possible, makes the insertion procedure achievable with minimal forces exerted on the patient's tissues This optimal result may in fact be a compromise on the optimal clinical configuration of the rods and the screws, in favor of a configuration that more readily enables a percutaneous robotic insertion procedure, this being a significant advantage over open back surgery, and thus a worthwhile tradeoff compared with the optimum screw and rod placement. Thus, if the clinically optimum configuration results in a rod shape which would require an open back surgical procedure to insert, a very minor amendment from that clinically optimum configuration, which may not have any significant effect on the efficiency of the surgical outcome, may enable the whole procedure to be performed minimally invasively, with the substantial advantages achieved thereby. These advantages to the subject may more than compensate for any such slight deviation from the optimal correction configuration. In addition, the inclusion of osteotomies to enable more amenable posture correction and less aggressively curved connection rods should also be taken into account.

A mathematical algorithm is used which enables optimal design of the rod shape to provide the best compromise to be achieved between optimal clinical correction, as outlined above, and ease of insertion of the rod robotically and minimally invasively. Solution of this problem is similar to that of the path planning problem solution, or the well-known "piano mover algorithm", in which an attempt is made to find the optimal method of moving a piano into a room through passages or stairways with a minimum number of motion steps, including a conclusion that it is not possible at all! One such example of such a path planning algorithm is an algorithm for the insertion of a body into a cavity, which is illustrated by the guiding of a surgical insert into a femur for hip joint replacement surgery, as described in U.S. Pat. No. 5,343,385 to L. Joskowicz and R. H. Taylor, for "Interference Free Insertion of a Solid Body into a Cavity". The method includes the iterative planning of the shape of the femoral insert, if during the step-wise insertion process, the program shows that the insert will become stuck in the femoral cavity due to surface interference, preventing further insertion progress.

The insertion process may be performed using a combination of linear and rotational motions to ensure that the distal end of the inserted rod follows the predetermined path between the heads of the pedicle screws. All possible path plans are reviewed in the software of the system controller, to ascertain the optimum quadruple combination of (a) screw head position,
(b) screw angle of orientation,
(c) rod shape in three dimensions, and
(d) insertion path procedure The possible inclusion of a fifth criterion may also be considered, namely:

(e) surgical correction of specific vertebrae by osteotomy.

Each of the five variables has its parameter range limited by the clinical and mechanical conditions required for the procedure and permitted by the robotic system. The limitation in the lateral position and the orientation of a pedicle screw is determined by the pedicle itself, which, since it is small and has a very limited path envelope into which a screw can be safely and sturdily inserted without breaking out of the cortical bone structure, is usually the most stringent criterion to be applied to the insertion procedure. Therefore, there is little iterative variation available for these screw parameters. Slight positional and rotational motion of the vertebrae themselves is possible, accomplished during the insertion process by manipulation of the pedicle screw towers as the rod front end reaches the particular pedicle screw head. One such tower 18 is shown still connected to the pedicle screw head at the top end of the rod. The problem can be simplified by essentially converging onto only two major criteria which have to be contended with, namely the height and angular orientation of the pedicle screw and the rod shape in three dimensions, and these variables must be iteratively adjusted in order to provide a shape which allows the robotic insertion procedure of the rod to be achieved in the simplest and most trauma free procedure.

In general, in such an entry procedure, a further desired configuration of the planned rod profile is that it should include as few as possible points of inflexion, if at all, since manipulation of the rod sequentially in two oppositely directed trajectory segments or in differently oriented planes will require rotation of the rod, and such a rotation will apply sideways forces to the tissues in which the rod is already embedded. Limited rotations are both acceptable and often necessary for most practical insertion trajectories, but beyond a certain level of rotation, unacceptable trauma may result to the tissues. One main criterion for defining the ease of insertion can be understood to mean selection of a path that provides least trauma to the tissue, while still being enabled by the robotic range of motion available.

The method for treatment of each lateral side of the spine may advantageously involve the use of a global spinal alignment program to generate an overall preoperative surgical plan for correcting the curvature defects, which may also include osteotomy surgery on selected vertebrae.

Figure 2:
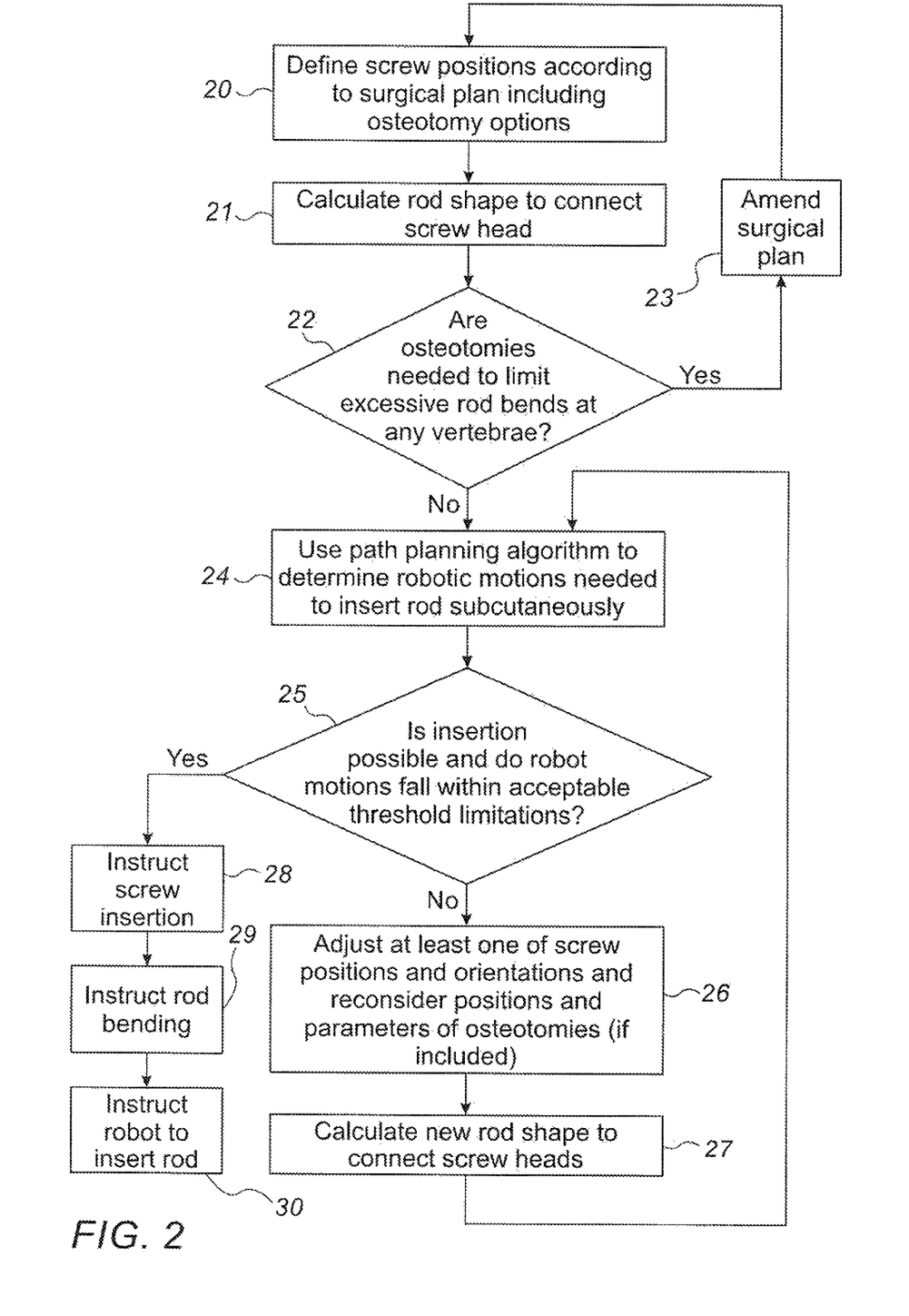
FIG. 2 shows one exemplary method for determination of the best configuration for minimally invasive treatment of spinal curvature, using robotically maneuvered connection rod insertion.

Reference is now made to FIG. 2, which is a flow chart illustrating the steps of one exemplary method for implementation of that plan (shown for one side of the spine), according to methods described in this disclosure:

In step 20, the surgeon's preoperative surgical plan is used to define the screw positions providing the optimal correction of the patient's deformity. This surgical plan needs to be reconciled with two other considerations, namely, the preference to avoid osteotomies if possible, and the need to use a rod having a shape with limited bend configurations that enable insertion of the rod percutaneously. In the event that such a rod configuration cannot be obtained readily according to the procedure described in this method, then the plan may need to take into account the possible need for performing osteotomies on selected vertebrae, in order to relieve the need for unnecessarily sharp bends in the connecting rod at any locations along the region of the spine to be treated. Such bends could make the rod impossible to insert, and could exert excessive forces on the pedicle screws or the relevant vertebra.

In step 21, the rod shape for connecting the screw tulips is calculated.

In optional step 22, the surgeon or user may determine whether the preoperative surgical plan has resulted in a calculated rod shape having convolutions or bends beyond a predetermined level, and determining whether correction using a less aggressively curved connection rod could be achieved by performance of an osteotomy at one or more vertebral levels. This determination is consistent with the generally accepted view that an osteotomic procedure performed on a specific vertebrae is a useful procedure to avoid the need for a sharply bent correction rod at any other region of the spine, since in such a region, the forces applied by the correction rod on the vertebral screws will be high, thereby possibly compromising the integrity of the anchoring of the screw at that or those vertebrae.

In step 23, if it is indicated in step 22 that one or more osteotomy be performed, the preoperative surgical plan is amended accordingly, and steps 20 and 21 are performed again iteratively to provide an amended rod shape. Thus, in step 23, at least one attempt is thus made to avoid or reduce any osteotomies by adjusting the starting parameters of the iterative routine. If after further iterations, it becomes evident that the loop involving steps 20 to 23 does not close with a negative result, and osteotomies cannot be avoided, then the procedure is continued including osteotomy options, as indicated in step 20.

In step 24, a path planning mathematical algorithm is used to determine the robotic motions required to insert the rod percutaneously, using lateral deflections, rotations and longitudinal motion of the proximal end of the rod, in order to pass its distal end through the required openings in the screw heads. The rod may deviate slightly from the screw head, but at the end of the insertion phase, it should be either through or located just above the open headed tulips, so that it can be readily pushed down into the tulip opening. Since this is a percutaneous procedure, the deviation cannot be significant, typically 2 mm. at most. As mentioned hereinabove, the application of force to the towers 18, enables slight motion of the vertebra, to correct any limited misalignment encountered.

In step 25, it is determined whether or not it is geometrically possible to thread the rod shape obtained in step 21 into position through the pedicle screw heads, by robotic insertion motions of the rod percutaneously, and if a solution is possible, whether the robotic motions of the rod fall within a predetermined threshold of acceptable insertion motion procedures, such as may be associated with the maximum lateral forces which the robotic insertion procedure should exert on the patient's tissues.

If an insertion path is found to be possible, and with the minimally desired insertion threshold parameters, then the method provides the robotic system in step 28 with the approval to insert the screws in the determined positions in the vertebrae, and in step 29 with the instructions to the rod bender to prepare a rod bent to the profile generated, and in step 30, with the instruction to the robot to insert the rod according to the robotic motions generated.

On the other hand, if the robotic motions do not provide a possible insertion solution, or if a possible solution does not fall within a predetermined threshold of acceptable insertion motion procedures, in step 26, adjustment is made of at least one of the position and angle of the screws within predetermined permissible limits, and a reconsideration of any planned osteotomies, including their number, position, and parameters, is made in order to attempt to reduce the extent or directions of bends in the rod.

In step 27, the planned shape of the rod is recalculated in three dimensions so that its new proposed profile connects the adjusted positions of the screw heads. The procedure then returns to step 24, where the path planning algorithm is again performed in order to determine the robotic motions required to insert the rod percutaneously.

The procedure then performs step 25 again, to determine whether the robotic motions of the rod enable a feasible entry path, and if so, whether that entry path falls closer to the predetermined threshold of acceptable insertion motion procedures.

This iterative procedure continues with further adjustments of the screw parameters in the directions previously used, and adjustment of the osteotomy parameters in the directions used in the previous iteration, until successful insertion is achieved together with the predetermined threshold of acceptable insertion motion procedures.

Performance of the above suggested procedure should thus enable minimally invasive robotic planning and insertion of vertebral correction rods, with the possible inclusion of a limited number of osteotomies.

As an alternative procedure, the above method may be adapted with the intention of minimizing the number of osteotomies needed, in which case the iterative procedure is amended accordingly to generate an insertion path which provides minimally invasive insertion and a minimal number of osteotomies, or with no osteotomies at all, but with possibly larger lateral correction forces applied by the rod on the pedicle screws, or with a longer correction region to enable the minimization of osteotomies by spreading the vertebral correction over a longer length of the spine.

Figure 3A:
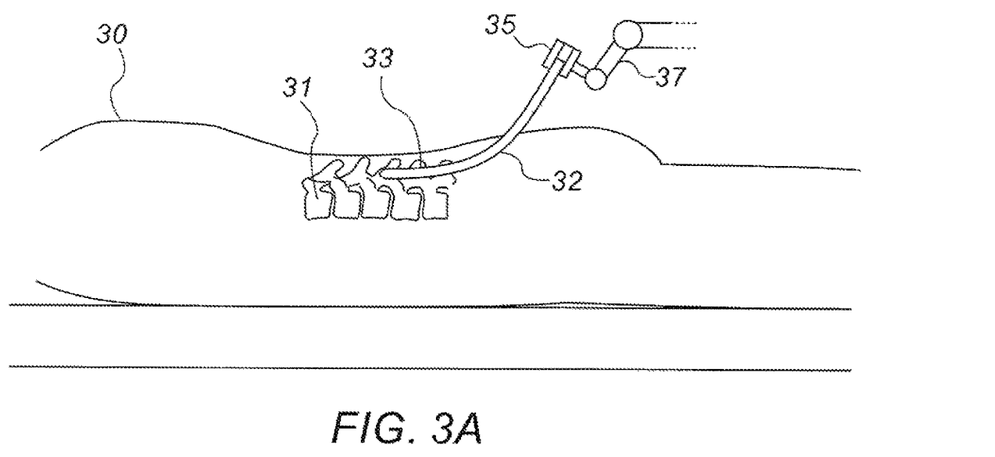
FIGS. 3A and 3B illustrate schematically the manipulation required for minimally invasive insertion of a vertebral connection rod, FIG. 3A showing robotic manipulation, and FIG. 3B showing a system using manual manipulation and a tracking system to define the pose of the rod.
Figure 3B:
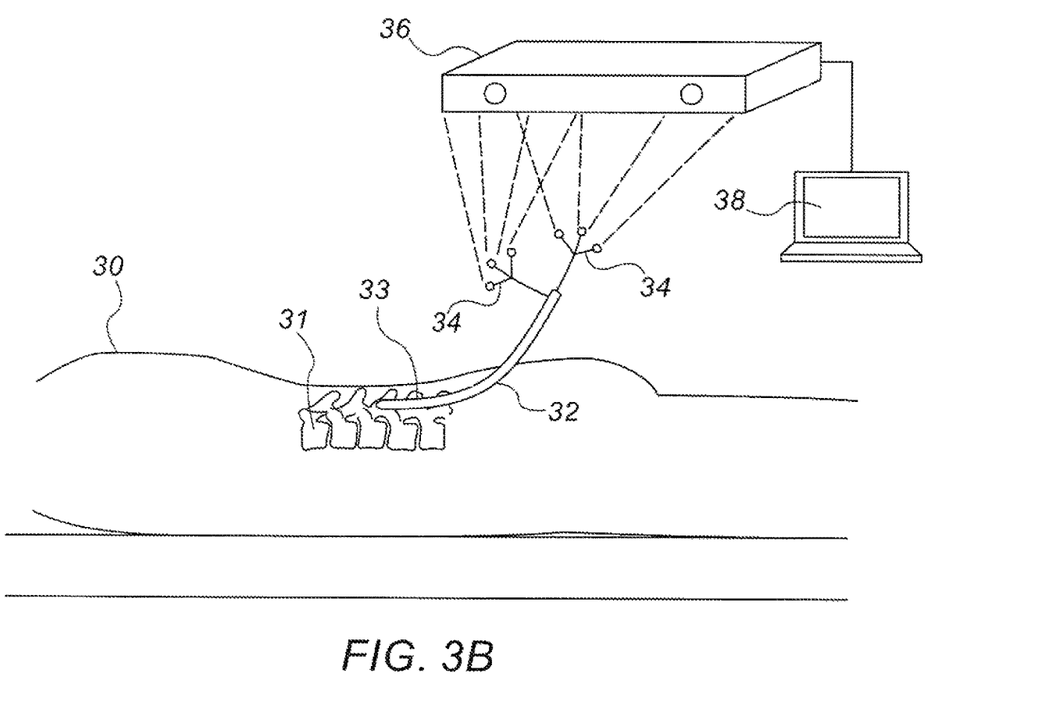

Reference is now made to FIGS. 3A and 3B, which illustrate schematically the manipulation required for minimally invasive insertion of a vertebral connection rod. FIG. 3A shows the use of a robot in manipulating the rod into its position. In this robotic implementation, the patient 30 is shown lying on the operating table and a number of vertebrae 31 are shown schematically with a connection rod 32 partly inserted through a number of the pedicle screw heads 33. A robotic actuation arm 37 is shown gripping the proximal end 35 of the rod, so that sequential movements of the robotic arm 37, enable insertion of the rod minimally invasively. The arm is shown as part of a floor or bed mounted robot, whose position relative to the patient 30, must be maintained in order to preserve the registration between the robot coordinate system and the preoperative plan images of the patient. However, a miniature bone-mounted robot can also be used for this purpose, provided it has a sufficiently large operating envelope to enable the completion of the whole of the insertion path.

In FIG. 3B, there is shown an alternative method of minimally invasive insertion of a vertebral connection rod, which can be accomplished using manual manipulation on the part of the surgeon. The implementation of FIG. 3B is used instead of the use of the robotic insertion process of FIG. 3A. The above described iterative planning of the shape of the rod and the longitudinal, orientational and rotational steps for inserting the rod remain unchanged. The method of FIG. 3B only describes a method of performing the insertion of the preplanned rod, without the need of a programmed robotic procedure. However, the preplanned motions and rotations, as determined by the exemplary method of FIG. 2 for instance, still have to be performed in a manner which maintains the data regarding the position and rotational orientation of the rod, so that insertion is performed correctly according to the predetermined plan.

In the exemplary system described in FIG. 3B, a navigation tracking system is used in order to determine the position and orientation of the rod as it is inserted. Many such types of navigation systems are known, including optical, ultrasound, and RF systems, and the optical tracking arrangement shown in FIG. 3B is not intended to limit the method to any specific type of navigational system. In the implementation shown in FIG. 3B, as in FIG. 3A, the patient 30 is shown lying on the operating table and a number of vertebrae 31 are shown schematically with a connection rod 32 partly inserted through a number of the pedicle screw heads 33. The position and rotational status of the rod is determined by means of LED beacons 34 disposed on the proximal end of the rod, in specific locations, which defines the spatial 3 dimensional position of the rod relative to the LED beacons. The position and orientation of the LED beacons 34 are determined by a navigation tracking camera 36, situated above the operating table, preferably in a position where the operating room staff will not obstruct direct view of the beacons 34 on the rod from the navigation system camera 36. This tracking camera can operate on a triangulation basis or using image processing, or by any other method known in the art, and can use its control system (not shown in FIG. 3A or 3B) to display the status of the position and orientation of the connection rod 32 on a display monitor 38. The navigation system may also receive inputs regarding the desired trajectory of the connection rod 32, as determined by the insertion software controller, such that the desired position and orientation and the actual position and orientation can be compared. Alternatively, the next insertion step required can be indicated to the surgeon by means of aural signals, or by any other suitable means such as a dedicated array of lights indicating movement direction required for the next step. The surgeon can grip the proximal end of the connection rod 32, and as each insertion step is performed according to the output of the software path planning system, the position and orientation of the end of the rod is determined by the tracking system, and the surgeon is able to follow on the tracking system display, how close his/her insertion of the rod is following the intended insertion path. The various software accessories can assist the surgeon's insertion steps, preferably by displaying on the system monitor or by issuing spoken instructions, how to make the correct motion steps in order to achieve the desired insertion trajectory of the rod. As previously mentioned, it is also possible to insert the rod minimally invasively by using repeated X-ray fluoroscope images to determine the position of the rod as it proceeds. The use of the navigational tracking shown in FIG. 3B, on the other hand, enables the minimally invasive insertion to be performed manually without the need for X-ray fluoroscope images.

All of the above described methods thus substantially reduce the trauma of currently used, open back surgical spinal correction procedures, and should also increase the accuracy of the correction procedure achieved. The method can be performed in coordination with the methods for global spinal alignment, as described in the above mentioned co-pending U.S. Provisional Patent Application Ser. No. 62/240,751, for "Global Spinal Alignment Method" having common inventors with the present application.

Figure 4:
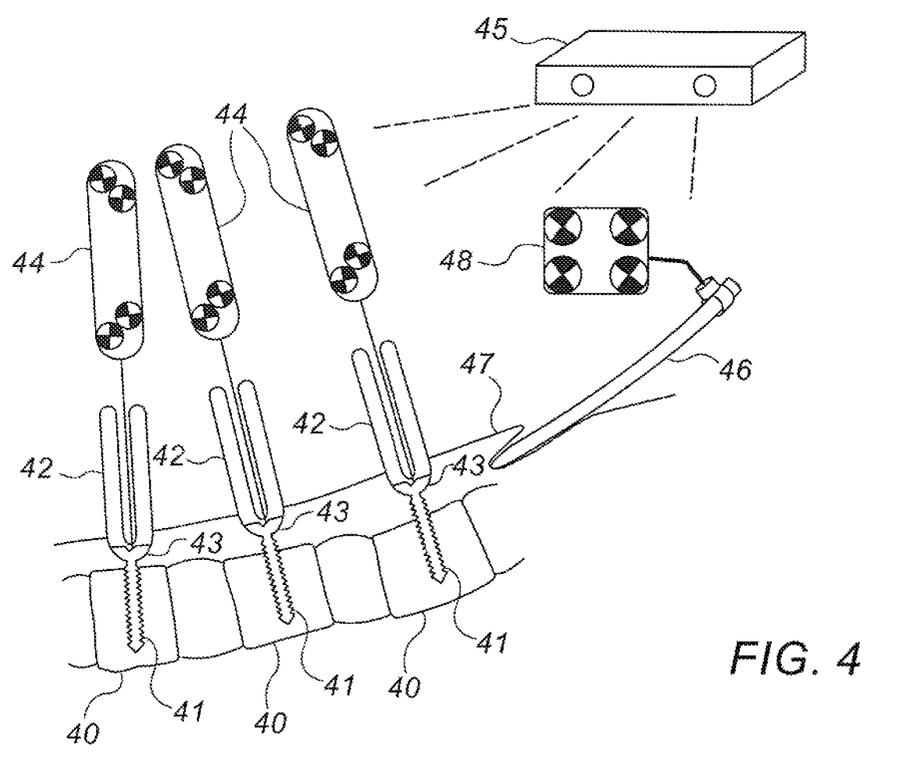
FIG. 4 illustrates schematically an extension of the system of FIG. 3, in which the tracking system also determines the position and orientation of the pedicle screws heads, such that the whole insertion procedure can be followed on a monitor and corrections to the rod trajectory can be made in real time.

Reference is now made to FIG. 4, which shows an extension of the implementation shown in FIG. 3B, in which not only is the position and orientation of the rod known, but the same navigational tracking system is used to determine the position and orientation of each of the pedicle screws or the towers that holds the screws. This enables the surgeon to follow in real time, the position of the leading end of the rod as it approaches each pedicle screw tulip, and to assist in the positioning of the rod over the tulip of each screw, such that the threading of the rod into the desired position may be performed manually or robotically.

In FIG. 4, there is shown schematically a section of the subject's spine, showing three adjacent vertebrae 40, into each of which a pedicle screw 41 has been inserted. A tower 42 is shown mounted on top of each of the pedicle screw tulips 43. Each of the pedicle screws or the towers has attached to it a marker 44, whose position and orientation in three dimensions can be detected by the camera 45 of a navigation tracking system. The vertebral connection rod 46, is shown being inserted through an incision in the subject's skin 47, and it too is fitted with a marker 48, to enable the position and orientation of the rod to be determined by the camera 45 of the navigation tracking system. The geometric shape and configuration of the rod is known from its production parameters, such that if the marker positions are known, the three dimensional spatial coordinates of every point along the rod are also known. A system and method by which this can be determined for any shaped rod, is described hereinbelow in connection with the implementation of FIG. 5. The signals obtained by the navigation tracking system camera, indicating the three-dimensional positions of the rod and of each of the pedicle screws, is processed by the control system (not shown in FIG. 4), and according to one implementation, a virtual model of the rod and of the position of the pedicle screws can be displayed on the system monitor. The surgeon can then manipulate the rod in space as it is inserted subcutaneously into the subject's spinal region, while viewing on the monitor exactly where and at what angle the rod is, relative to the pedicle screw tulips. This enables the entire insertion process to be performed accurately without robotic guidance, and without the need for multiple X-ray fluoroscopy images, with its associated radiation. Alternatively, this implementation can also be used to execute a robotic insertion, in which the position and orientation outputs obtained from the navigational tracking system are processed to provide real time instructions to the robot controller (not shown in FIG. 4) for the robotic movements that need to be made for each step of the insertion process.

Figure 5:
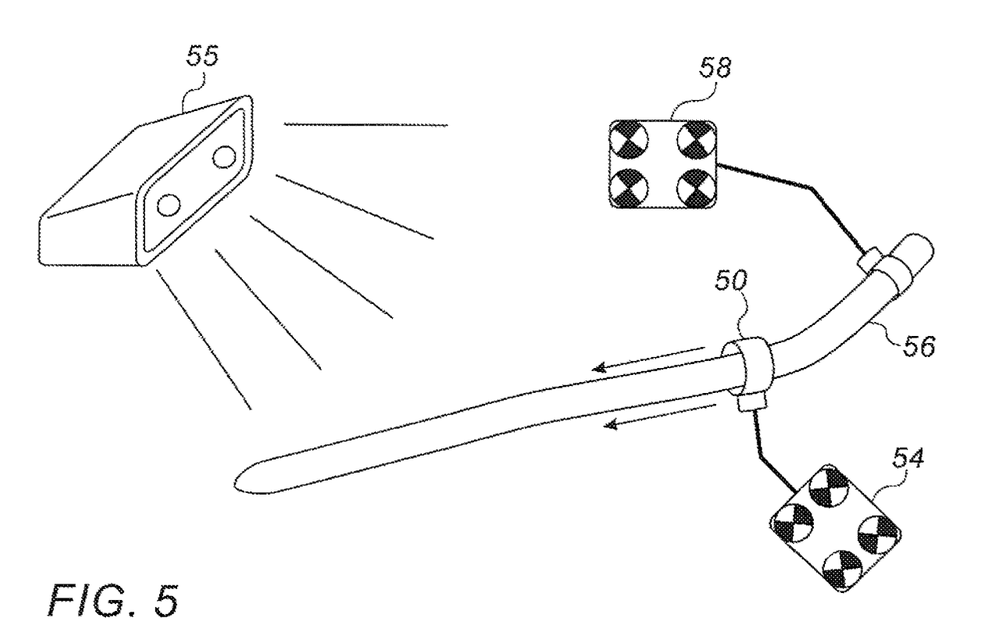
FIG. 5 illustrates schematically a system and method for determining the three-dimensional characteristics of a connecting rod, whose three-dimensional geometric shape is not known in advance.

Reference is now made to FIG. 5, which illustrates a system and method for determining the three-dimensional characteristics of a connection rod 56, whose three-dimensional geometric shape is not known in advance with any precision. Such a situation could arise when a rod is bent manually in the operating room, and the surgeon wishes to know its exact shape in order to determine its suitability for use in a specific calculated pedicle screw arrangement, or how to adjust its shape to improve its suitability for that specific arrangement. A sliding collar 50 is provided, that can freely slide down the length of the rod. The sliding collar is equipped with a marker device 54, whose position and orientation can be determined by the navigation tracker system camera 55. The collar 50 must be of sufficient length and having a sufficiently tight fit on the rod that its orientation is effectively equal to the orientation of the rod over which it slides, i.e. that it is co-axial with the section of rod on which it is positioned. As the collar is slid down the length of the rod 56, the control system (not shown in FIG. 5) continuously determines the orientation of the collar at each location down the rod. Since the pose of the collar 50 mimics the angle of orientation of the rod, a full sweep of the collar from one end of the rod to the other provides a complete representation in three dimensions of the spatial position and orientation of the rod 56, thereby fully characterizing the rod over the whole of its length.

The above described apparatus only operates correctly if the rod is stationary, such as when it is lying on a table, since the rod position must not change relative to the position of the navigation tracking camera. However, a more common situation occurs in the operating room when the surgeon is holding the rod in his hands, such as often having bent it with the appropriate tools, and he wishes to know quantitatively the three-dimensional shape of the rod, to determine whether it is appropriate for the surgical plan intended. In order to enable the rod shape to be determined in such a situation, it is necessary to determine the three dimensional position of the rod also, and this can be done by equipping the proximal end of the rod with a marker 58, rigidly fixed to the rod, and whose position and orientation can be determined by the same navigation tracker system camera 55, such that the position and orientation of the proximal end of the rod 56 is known at all times, regardless of motion of the rod. Using this data, the position and orientation of each point along the rod length measured by the sliding collar is then known relative to the rod, and not only relative to free space. Although the most convenient configuration is to have the marker 58 attached to one end of the rod, such that the sliding collar 50 can be moved continuously from one end of the rod to the other, it is to be understood that the marker 58 may be attached at any other convenient location in the rod, in which case the sliding collar had to track along the length of the rod into sections. However, the processing and control system is able to handle this data and to determine the configuration of the whole length of the rod.

In either of the implementations of FIGS. 4 and 5, the markers may be active, with a passive detection camera system, or passive with an active detection camera system. Active markers may include luminous beacons such as LEDs, detected by an optical camera facility, or ultrasonic or RF or acoustic emitters, with corresponding detection sensors, while passive markers could be markers with definable features whose location and orientation can be determined by a remote ranging transmitter and receiver, including a triangulation vision camera, or any other suitable tracking system known in the art.

It is appreciated by persons skilled in the art that the present invention is not limited by what has been particularly shown and described hereinabove. Rather the scope of the present invention includes both combinations and subcombinations of various features described hereinabove as well as variations and modifications thereto which would occur to a person of skill in the art upon reading the above description and which are not in the prior art.

The invention claimed is:

1. A method of planning an intervertebral rod insertion procedure, comprising:
   using a preoperative surgical plan to define positions and orientations for inserting screws into vertebrae of a subject, each of the screws having a head;
   calculating a shape of a rod that will connect the heads of the screws;
   determining, using a path planning algorithm, whether manipulation of a proximal end of the rod having the calculated shape enables a distal end of the rod to pass sequentially through the heads of the screws;
   when the distal end of the rod can be passed sequentially through the heads of the screws:
      providing instructions for insertion of the screws in the defined positions and orientations,
      providing information for forming the rod having the shape, and
      providing instructions for insertion of the rod; or
   when the distal end of the rod cannot be passed through the heads of the screws:
      adjusting in the plan, at least one of the position and orientation of at least one of the screws in order to moderate bends in a path between the heads of the screws, and recalculating the shape of the rod to match any adjusted position and orientation of the at least one screw;
      using the path planning algorithm on the rod having moderated bends to determine whether the rod can be passed through the heads of the screws; and
      repeating the steps of adjusting the screw positions, and recalculating the rod shape, until the rod acquires a planned shape that enables it to be inserted between the heads of the screws by longitudinal manipulation of the rod from its proximal end.

2. A method according to claim 1, wherein the step of determining whether manipulation of the proximal end of the rod having the calculated shape enables the distal end of the rod to be passed through the heads of the screws, includes broadening a range of rod shape which can be passed through the heads of the screws by enabling adjustment of a position or orientation of at least one of the vertebrae.

3. A method according to claim 1, wherein a criterion of enabling the distal end of the rod to be passed through the heads of the screws includes possibility of proposing adjustment of a position or orientation of at least one of the vertebrae.

4. A method according to claim 1, wherein the plan further includes an optional use of osteotomies on selected vertebrae to enable the moderating of bends in the rod.

5. A method according to claim 4, further comprising selecting at least some of a number, position, and parameters of the osteotomies to reduce a diversity of bend directions in the rod.

6. A method according to claim 1, wherein the moderating of bends in the rod comprises reducing at least one of an extent and a diversity of direction of the bends.

7. A method according to claim 1, further comprising the step of providing instructions to a robot control to manipulate is the proximal end of the rod, such that the rod can be inserted robotically.

8. A method according to claim 1, further comprising the step of providing instructions to manipulate the proximal end of the rod manually using information from X-ray fluoroscopy images to enable defining a position of the rod during insertion.

9. A method according to claim 1, further comprising using a navigational tracking system adapted to enable determination of the a position and orientation of the proximal end of the rod during insertion.

10. A method according to claim 1, wherein if the distal end of the rod can be passed through the heads of the screws, the method further comprises determining whether the step of inserting the rod involves motions of the rod within a predetermined threshold of acceptable insertion motion procedures.

11. A method according to claim 1, further comprising the step of determining maximum lateral forces which the insertion procedure would exert on the subject's tissues.

12. A system for minimally invasive insertion of an intervertebral rod, comprising:
  a robot whose position is known relative to a subject's vertebrae; and
  a control system adapted to receive information about a position of a head of each of a plurality of rod-clamping screws, each screw to be inserted at a defined position and orientation into a subject's vertebrae according to a preoperative surgical plan, and information about a shape of a rod calculated using the preoperative surgical plan, the calculated shape being such that the rod can pass through the heads of the screws, the control system being further adapted to:
    utilize a path planning algorithm to determine whether manipulating a proximal end of the rod having the calculated shape, enables the distal end of the rod to be passed sequentially through the heads of the screws;
    when the distal end of the rod can be passed through the heads of the screws, instructing the screws to be inserted in the defined positions and orientations, and instructing the robot to insert the rod by longitudinal manipulation of the rod from its proximal end; and
    when the distal end of the rod cannot be passed through the heads of the screws, adjusting at least one of the position and an orientation of at least one of the screws in order to moderate bends in a path through the heads of the screws.

13. A system according to claim 12, wherein when the distal end of the rod cannot be passed through the heads of the screws, the control system is further adapted to:
  adjust the information about the rod shape to include an updated shape based on the adjusted position and orientation of the screws;
  use the path planning algorithm to determine whether, with the updated shape, the rod can be passed through the heads of the screws; and
  repeat the steps of adjusting at least one of the position and orientation of at least one of the screw, and adjusting the information about the rod shape, until the updated shape enables the robot to insert the rod through the heads of the screws by longitudinal manipulation of a proximal end of the rod.

14. A system according to claim 12, wherein at least one of the subject's vertebrae incorporates a tower adjustment device to enable adjustment of a position or an orientation of the at least one of the subject's vertebrae, such that the control system also enables the broadening of a range of rod shapes which can be passed through the heads of the one or more screws.

15. A system according to claim 12, wherein the moderating of bends in the path comprises reducing at least one of an extent and a diversity of direction of the bends.

16. A system according to claim 12, further comprising a navigational tracking system adapted to enable determination of a position and orientation of the proximal end of the rod during insertion of the rod.

17. A system according to claim 16, wherein the rod comprises at least one marker attached with a predetermined pose on the proximal end of the rod, the marker being such that its pose can be tracked by the navigational tracking system during insertion of the rod.

18. A system according to claim 12, wherein the control system is adapted to receive information about a position of the rod during insertion of the rod using X-ray fluoroscopy images.

* * * * *

UNITED STATES PATENT AND TRADEMARK OFFICE
CERTIFICATE OF CORRECTION

PATENT NO. : 10,849,691 B2
APPLICATION NO. : 16/312296
DATED : December 1, 2020
INVENTOR(S) : Edo Zucker, Moshe Shoham and Yuval Chen It is certified that error appears in the above-identified patent and that said Letters Patent is hereby corrected as shown below:

In the Claims

Claim 2, Column 16, Line 64, delete "shape" and insert --shapes--

Claim 3, Column 17, Line 3, delete "heads of the screws includes possibility of proposing" and insert --heads of the screws includes a possibility of proposing--

Claim 7, Column 17, Line 18, delete "is the proximal end of the rod, such that the rod can be" and insert --the proximal end of the rod, such that the rod can be--

Claim 9, Column 17, Line 27, delete "determination of the a position and orientation of the" and insert --determination of a position and orientation of the--

Claim 12, Column 17, Line 45, delete "vertebrae" and insert --vertebra--

Claim 12, Column 18, Line 1, delete "calculated shape, enables the distal end of the rod" and insert --calculated shape enables a distal end of the rod--

Claim 12, Column 18, Line 11, delete "position and an orientation of at least one of the" and insert --position and orientation of at least one of the--

Claim 13, Column 18, Line 24, delete "screw" and insert --screws--

Signed and Sealed this
Thirtieth Day of March, 2021

Drew Hirshfeld
*Performing the Functions and Duties of the
Under Secretary of Commerce for Intellectual Property and
Director of the United States Patent and Trademark Office*